United States Patent [19]

Pappas

[11] Patent Number: 5,683,467
[45] Date of Patent: Nov. 4, 1997

[54] PROSTHESIS WITH ARTICULATING SURFACE STRESS REDUCING CONTACT EDGE

[75] Inventor: Michael J. Pappas, Stuart, Fla.

[73] Assignee: Biomedical Engineering Trust I, N.J.

[21] Appl. No.: 345,302

[22] Filed: Nov. 28, 1994

[51] Int. Cl.⁶ ........................................... A61F 2/38
[52] U.S. Cl. ........................................... 623/20
[58] Field of Search ................... 623/18–23; 403/41

[56] References Cited

U.S. PATENT DOCUMENTS

| 5,387,240 | 2/1995 | Pottenger | 623/20 |
| 5,489,311 | 2/1996 | Cipolletti | 623/20 |

OTHER PUBLICATIONS

Pappas, et al. "Contact Stresses in Metal–Plastic Total Knee Replacements: A Theoretical and Experimental Study", Jan. 23, 1986, pp. 1–7.

Primary Examiner—Michael J. Milano
Attorney, Agent, or Firm—Anthony J. Casella; Gerald E. Hespos

[57] ABSTRACT

A prothesis tibial bearing of thermoplastic material has a planar surface which engages the mating planar surface of a second prothesis component such as the tibial platform. The typically metal platform edge wipes across the inner surface region of the bearing causing deformation of the bearing surface. This deformation causes stress magnification in the bearing at the platform edge region. The edge region of the platform planar surface is tapered to provide a gradual curved ramp between a relatively small corner radius at the platform edge and the platform planar surface, the tapered region being tangential to the edge radius and to the platform planar surface. The stress concentration increase at the edge region of the bearing is reduced at the platform edge region to below 100% and preferably to about 25% of the stress value between the bearing and the platform in the region interior the platform edge. The tapered surface region is preferably a curvature of tangential contiguous radii tangent to the platform planar surface, but may be planar.

24 Claims, 7 Drawing Sheets

PROSTHESIS WITH ARTICULATING SURFACE STRESS REDUCING CONTACT EDGE

BACKGROUND OF THE INVENTION

Field of the Invention

This invention relates to protheses with articulating engaged surfaces, and more particularly, to articulating surfaces in which the edge of one prothesis component surface engages the surface of a mating component.

Frequently in the articulation surfaces of artificial human or animal joints the edge of one of the surfaces will move across the surface of another (referred to herein as "edge wiping"). This occurs, for example, in a hip replacement joint where the truncation of the femoral head spherical surface produces an edge that wipes at least part of the articulating surface of the ultra high molecular weight polyethylene (UHMWPe) acetabular bearing. Another example includes a prosthesis in which the edge of an articulating surface of a metallic acetabular component wipes over the surface of a plastic femoral head.

The present inventor has observed and recognizes that where a surface edge of a first articulating surface of an articulating prothesis couple contacts an interior region of the second articulating surface of the couple, the compressive load in the second surface changes suddenly as the second surface loses contact with the first surface. This is because the compressive load produces deformation, i.e., strain, of at least one of the mating surfaces. But such strain can occur also with plastic to plastic contact and with metal to metal contact. The deformation terminates abruptly at the edge region of one surface of the couple where the edge region overlies an interior region of the other couple surface.

This sudden change in strain in the interior of the other couple surface produces a stress riser (stress magnification) in the prothesis material in the region of the edge contact. This is illustrated in FIG. 1. In FIG. 1, a representative prior art metallic-plastic articulating couple formed by prothesis 1 is illustrated showing a prothesis thermoplastic bearing 2 having a first surface 3 engaged with a second surface 5 of metal platform 4. When the bearing 2 exerts a compressive load on the platform 4, in direction 7, the stress contour curve 8 is generally uniform as shown in region-11 except for the edge region 6. The stress in edge region 6 is significantly higher than the stress in interior region 11, generally about a 400% increase in stress in the material, due to the abrupt change in strain δ in the edge region 6.

When the first surface 3 is metallic, this local increase in stress is not as important since the metallic surface is strong enough to endure this large increase in stress in a prothesis environment without significant damage. In a prothesis environment the motions between the articulating surfaces are relatively slow and the stresses negligible in comparison to the metal material strength properties. This results in negligible damage to the surfaces.

When, however, a metallic edge 9, such as on platform 4, wipes a surface of a thermoplastic member, such as surface 3 of bearing 2, a localized strain δ is produced which varies to a maximum relatively abruptly and which strain produces the stress increase at curve portion 10 in region 6. This stress increase portion 10 will usually produce greatly increased thermoplastic surface 3 damage in joint replacement articulations as the edge 9 of the one surface such as the surface 5 of platform 4 wipes over the mating surface such as surface 3 of bearing 2.

In contrast to the above analysis of the present inventor, those of ordinary skill in prosthesis design concluded differently in the observation of damage resulting in the plastic bearings of replacement joints where a plastic head is used with a metallic socket in which the edge of the socket wipes the surface of the plastic head. It is of general belief by those of ordinary skill in this art that the concave element of an articulating plastic-metal couple must be plastic, and the convex element must be metallic.

However, as observed by the present inventor as discussed above, the problem of surface damage of the thermoplastic component is not directly related to the issue of concavity or convexity. For example, if the articulation is incongruent, and there is no edge wiping effect, whether the convex surface is metallic or plastic does not substantially effect the maximum contact stress in the plastic. Often with incongruent contact, it is desirable to make the head of plastic and the socket of metal since, during articulation, the damaging peak loads would be spread over a larger plastic surface reducing the damaging effect of these loads on the plastic.

The present inventor was involved in the development of a shoulder prosthesis with a plastic head which was in incongruent contact with a metallic socket, a configuration which is superior to a similar design with a metallic head and a plastic socket. Yet the perception by those of ordinary skill in this art that the convex articulating surface element must be metallic was, and is, so pervasive that the device could not, and cannot today, be brought to market. Thus the edge wiping phenomenon as discussed above is not generally understood by those of ordinary skill in the prosthetic design art.

The utilization of the principle of edge strain/stress and resulting deformation and damage to an articulating surface according to an embodiment of the present invention provides an arrangement of articulating surfaces of a prothesis couple which takes into consideration the edge wiping effect providing an improved prothesis.

In a prothesis including a joint comprising first and second members each having a surface thereof articulating under load in contact with one another, the combination according to the present invention comprises a first member having a first surface and a second member having a second surface for engaging in articulating contact the first surface, the second surface having an edge, the second surface including the edge being under compressive load with the first surface-during the articulating contact, the compressive load causing the first member in the region of the second surface to exhibit a contact stress of generally a first value, the second surface having a gradual tapering region adjacent to and extending inwardly the second surface from the second surface edge a distance W so as to cause the first member to exhibit increased edge stress concentration in the region of engagement of the edge of the second surface with the first surface of a second value in the first member of no more than about twice the first value. As a result of the reduced edge stress concentration, the edge wiping generates a minimum of damage to the first surface especially when the first surface is of lower strength than the second surface.

In one embodiment, the second member is metal and the first member is a thermoplastic.

In a further embodiment the increased edge contact stress second value is about 25% greater than the first value.

In a prothesis including a joint comprising first and second members each having a surface thereof articulating under load in contact with one another in accordance with a further embodiment, the combination comprises a thermoplastic first member having a first surface and a second metallic member having a second surface for engaging in articulating contact the first surface, the second surface having an edge, the second surface including the edge being under compressive load with the first surface during the articulating contact, the second surface having a gradual tapering region adjacent to and extending inwardly the second surface from the edge a distance W so as to cause the first member to exhibit a gradual preferably uniform rate of change of deformation in the first surface in response to the compressive load with the second surface such that the deformation varies from essentially zero at the edge to a maximum at the planar second surface the distance W.

IN THE DRAWING

Figure 2:
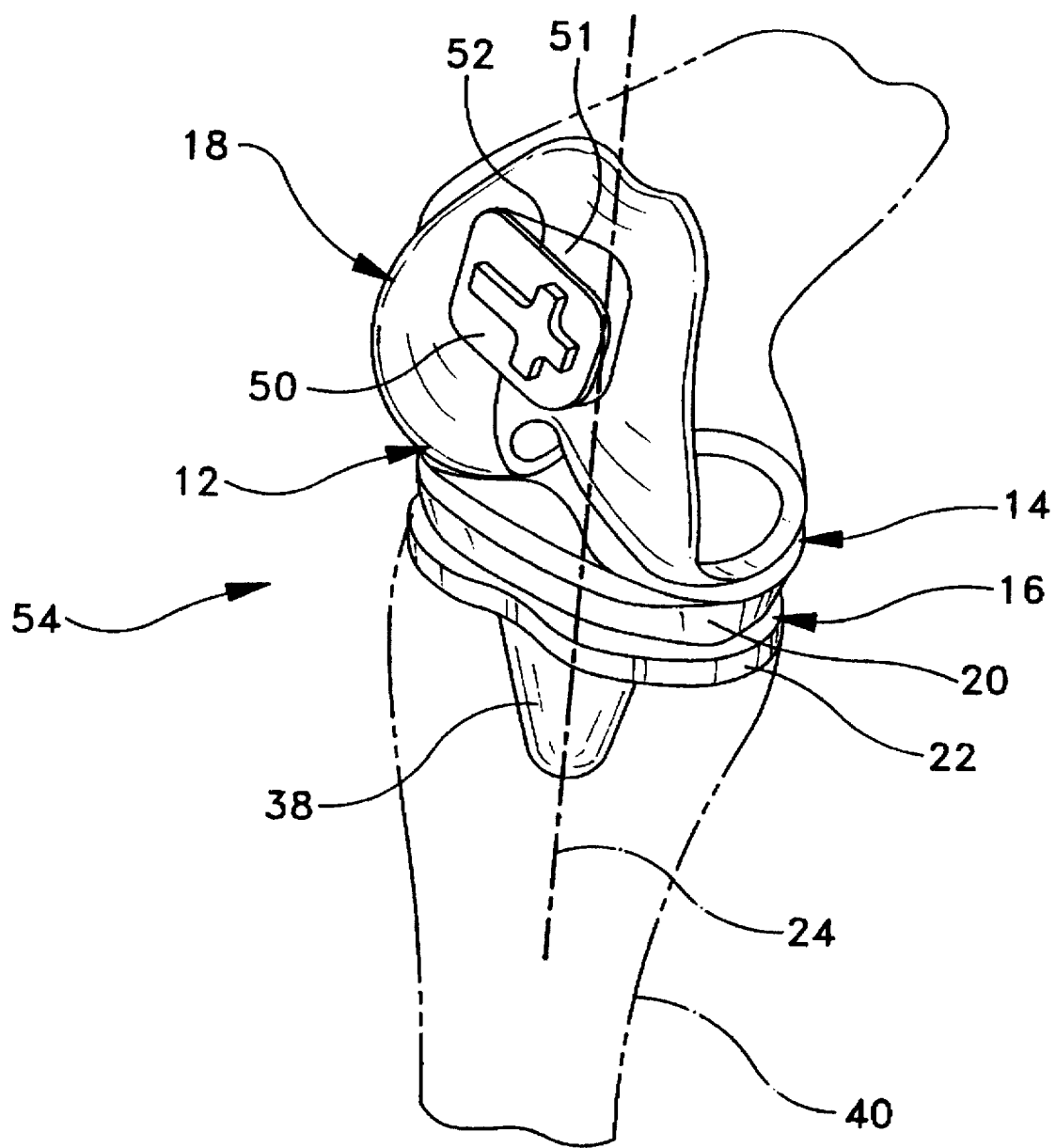
FIG. 2 is an isometric view of a knee and prothesis embodying the present invention.

Knee replacement 12, FIG. 2, is generally of known construction, except for the improvement to be described below. The details of the various components forming replacement need not be given herein. Replacement 12 comprises a femoral component 14, a tibial component 16 and a patellar component 18. The tibial component 16 comprises a tibial bearing 20 and a tibial platform 22 which are rotatable with respect to each other about axis 24.

Figure 3:
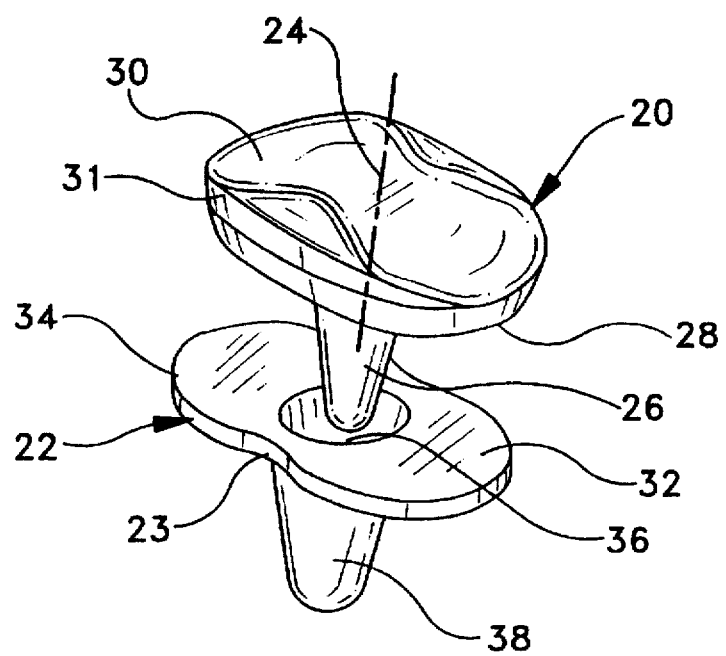
FIGS. 3 AND 4 are respective exploded and assembled isometric views of a bearing and platform assembly portion of the embodiment of FIG. 2.

The bearing 20, which is ultra high molecular weight polyethylene (UHMWPe), includes a depending conical stem 26, FIG. 3. The bearing 20 has a planar surface 28 for engaging a mating planar surface 32 of the tibial platform 22 and a bearing surface 30 for receiving the mating condyle of the femoral component 14. The bearing 20 has a peripheral edge 31.

The tibial platform 22, which is typically metal, of material known in this art, includes a platform member 23 which has planar platform surface 32. Surface 32 abuts the bearing 20 planar surface 28. The surface 32 has a peripheral edge 34. The platform 22 has a conical cavity 36 within conical stem 38 which is implanted in the tibia 40, FIG. 2. Cavity 36 receives the bearing 20 stem 26 along axis 24 defined by cavity 36 and stem 26. The bearing 20 rotates about axis 24 relative to the platform 22 via the engaged conical tibial stem 26 and platform cavity 36. Bearing surface 28 compressively engages platform surface 32 during this rotation.

The edges 31 of the bearing and 34 of the platform are irregular, elongated and somewhat oval in plan view. Rotation of the bearing 20 about axis 24 with respect to platform 22 results in the edge 34 portions 34' of the platform 22, FIG. 4, engaging and overlying corresponding interior portions of the planar surface 28 of the bearing 20.

Figure 4:
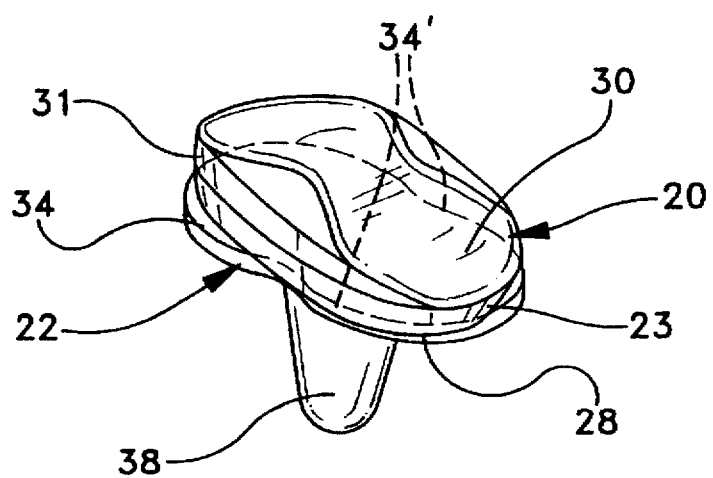

Compressive loads between the tibial bearing 20 and tibial platform 22 during articulation are borne by the engaged planar tibial bearing surface 28 and the planar tibial platform surface 32. During normal human activity, rotation of the tibial bearing 20 relative to the tibial platform 22 about axis 24 may result in the planar tibial bearing 20 surface edge 31 of the tibial bearing 20 overhanging the planar tibial platform surface edge 34 of the tibial platform 22 as shown in FIG. 4. Also, the edge 34' of the platform may overly the bearing surface 28. Such motion will produce an edge wiping effect and increase wear on the tibial bearing surface 28 if the tibial platform edge 34 were made in the conventional manner of FIG. 1.

Figure 1:
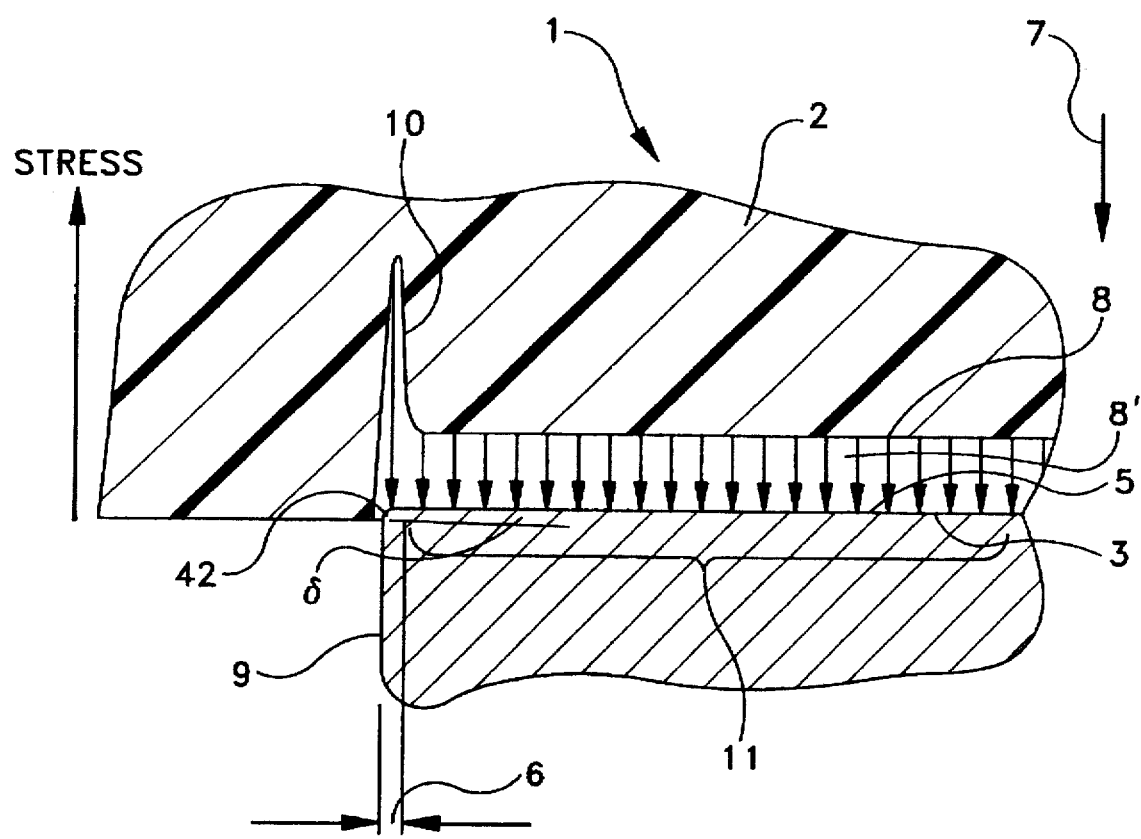
FIG. 1 is an illustration of prior art prothesis components in contact with each other including a stress contour graph useful for explaining the edge stress principles.

In FIG. 1, the platform 4 metallic edge 9 corner adjacent to the bearing 2 surface 3 has a relatively small radius 42. The relatively small radius 42 which is typically about 0.7 mm results in the compression stress contour 8 as discussed in the introductory portion. The increased stress concentration curve portion 10 at the region of radius 42, region 6, is undesirable. This stress may have a magnitude of about 400% the stress magnitude of the uniform portion 8' region 11 of the stress contour curve 8. The abrupt change in deformation (strain) $\delta$ of the bearing 2 at the edge 9 causes undue wear of the bearing 2 as the platform 4 rotates on the bearing planar surface 3. Surface 3 is no longer planar at the edge region of radius 42 due to the deformation $\delta$ in the softer thermoplastic bearing 2.

Figure 8:
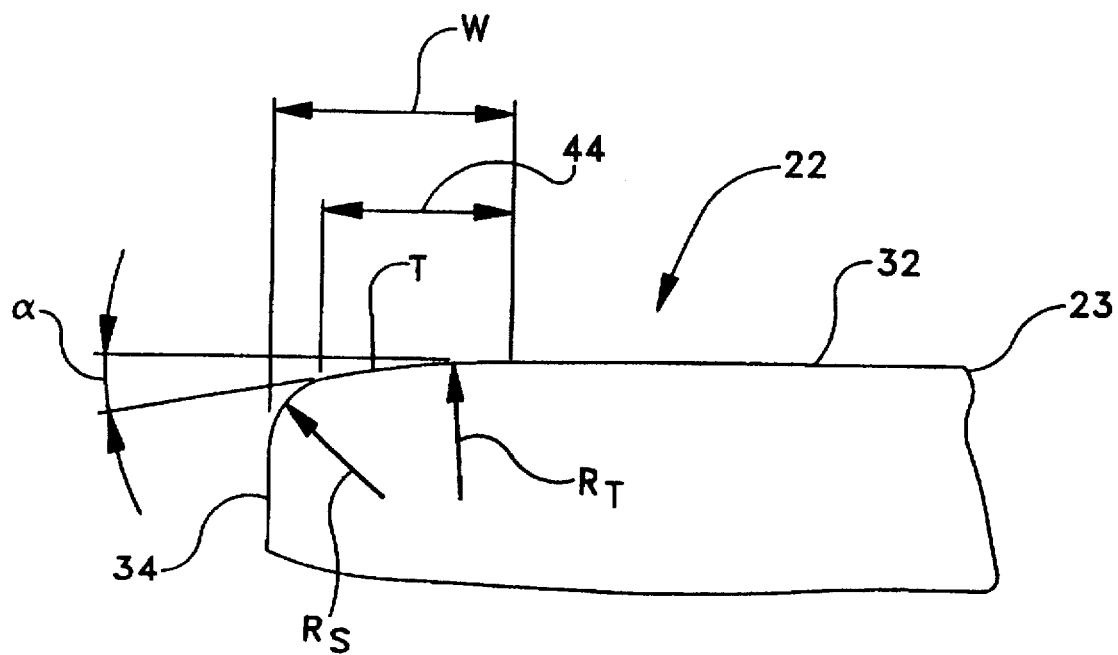
FIG. 8 is a side elevation sectional view of the platform of FIG. 5 useful for explaining further principles of the present invention.

In FIG. 8, planar tibial platform member 23 surface 32 according to an embodiment of the present invention has a tapered region 44 extending inwardly from edge 34 small radius $R_s$, it being recalled radius $R_s$ may typically be about 0.7 mm. Region 44 is inclined relative to the platform 23 planar surface 32 generally less than 10° and preferably considerably smaller. For example, the region 44 may extend inwardly from edge 34 a distance W which may by about 3.2 mm in one embodiment. In this embodiment the region 44 is defined by a relatively larger radius $R_r$, which may be about 50 mm.

The tapered surface T in region 44 is tangent to planar surface 32 and to the radius $R_s$ in this embodiment. In this case the angle $\alpha$ of surface T to the plane of surface 32 is much smaller than 10°. The width W and inclination of the tapered surface T may differ according to a given implementation. The width W and angle $\alpha$ may be determined empirically for a given implementation to minimize the undesirable edge wiping wear discussed above. The factors to consider are relative hardness of the two engaging surfaces and the anticipated load.

UHMWPe bearing material and typical metals employed for prothesis components such as a cobalt chromium alloy or a ceramic coated titanium alloy are employed in the present embodiment. Surface finishes are highly polished and smooth as is typical for such components as used in the prior art and thus are not a major factor in the edge stress condition. The load in the typical prothesis is assumed for normal human implementations and, therefore, is also not a major factor from prothesis to prothesis design. Also, the tapered surface T may be curved or planar, a curve being preferable. The curvature of the curve does not necessarily have to be formed by a single radius and a non-circular curve is preferred. Such a curve gradually slopes and merges into surface 32 tangentially and then increases in inclination relative to surface 32 as it tangentially approaches the radius $R_r$. Such a curve might be hyperbolic or a similar curve. In this case the angle α is only a generalized average value of the curved surface T.

Figure 5:
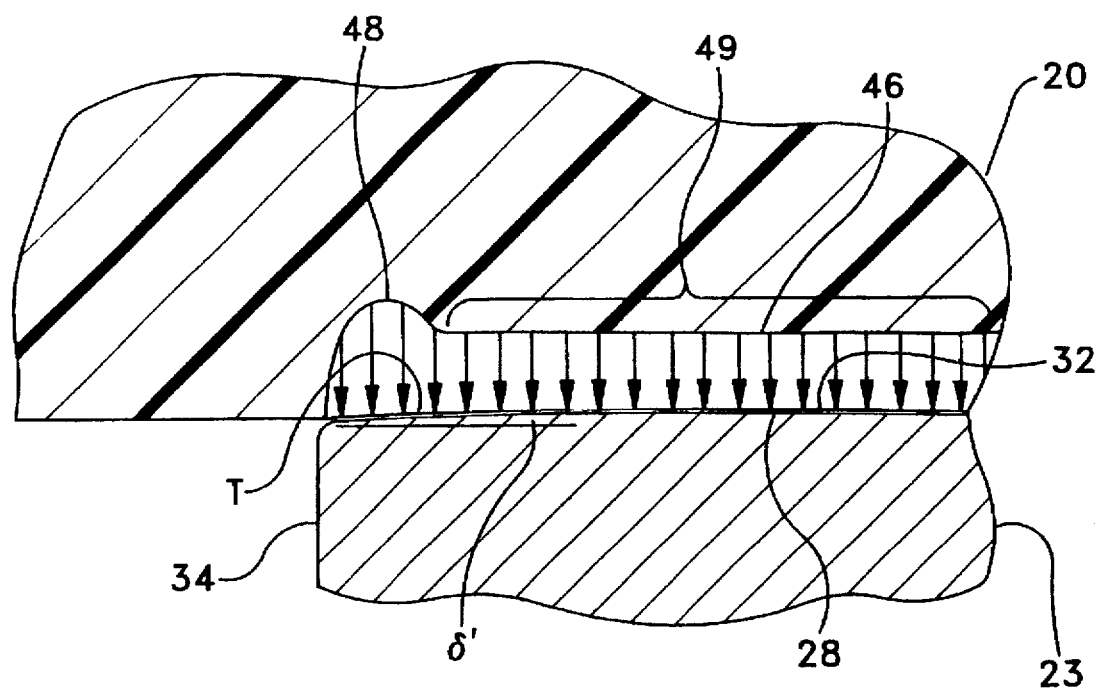
FIG. 5 is an illustration of prothesis components according to an embodiment of the present invention useful for explaining some of the principles of the present invention.

FIG. 5 illustrates a stress curve 46 having a stress concentration portion 48 for the platform member 23 and bearing 20. Region 49 has a substantially uniform stress as represented by the horizontal line portion of curve 46 parallel to surface 32. The tapered surface T produces a maximum deformation δ' in the bearing 20 which deformation is not abrupt at the area adjacent the edge 34 as occurs in the prior art of FIG. 1. It should be understood that the drawing is not to scale and the actual inclination of tapered surface T is much less than that illustrated, which inclination is exaggerated for purposes of illustration. The deformation δ' is gradual and tapers slightly from essentially a minimum or negligible value at the edge 34 to the maximum value in the interior region 49 of platform 23 surface 32 and bearing 20 surface 28 a distance W (FIG. 8). The stress concentration in the region of curve portion 48 of curve 46 is a maximum of about 25% greater than the average value of the stress in the remaining portion of curve 46.

Figure 9:
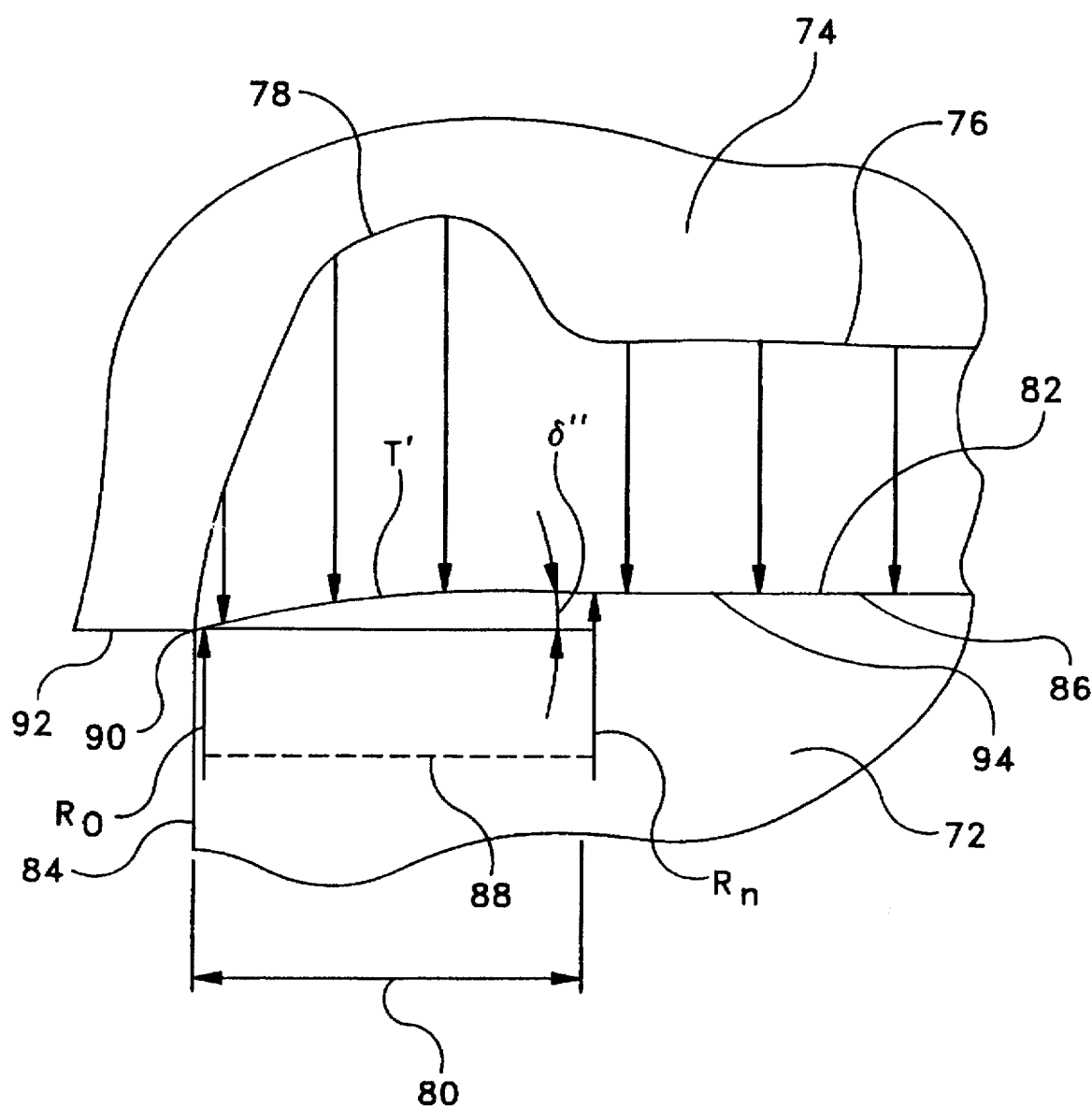
FIG. 9 is an illustration of prothesis components according to a further embodiment of the present invention useful for further explaining the principles of the present invention.

In FIG. 9, a preferred embodiment of prothesis component platform 72 is shown in stress contact with a thermoplastic bearing 74. The stress contour is shown by curve 76 having a stress concentration curve portion 78 in region 80. The tapered surface T' merges with the platform 72 planar surface 82 in a radius $R_n$. However the tapered surface T' at platform edge 84, which edge is generally normal to and in contact with surface 86 of bearing 74, has no radius corresponding to radius $R_r$, FIG. 8.

In this embodiment, the surface T' comprises a curvature of a series of contiguous tangentially coupled radii $R_o$ to $R_n$ as represented by dashed line 88. Thus the surface T' blends in with the plane of surface 82 by radius $R_n$ but merges in a relatively sharp corner 90 with edge 84. For practical purposes the corner 90 is broken to remove burrs and to round it somewhat to remove the sharpness thereof in the interest of safety to persons handling the platform 72. Otherwise for purposes of minimizing edge wiping damage, the corner 90 need not have a radius, including the relatively small radius $R_s$ of FIG. 8. Consequently, the load, and thus, the deformation δ", in the softer plastic bearing 74 varies gradually from the edge 84 to the planar portion of surface 82 regardless the presence of an edge radius at corner 90. This results in reduced stress concentration at the edge region in comparison to the high stress concentration with the non-linear and abrupt localized deformation δ (strain) in the prior art arrangement of FIG. 1.

The relatively small radius $R_s$ is not needed because the compressive stress curve portion 78 is reduced in value without that radius. No edge radius on the platform at corner 90 is therefore necessary to minimize the wear at the platform edge 84. The stress concentration at the edge region 80 is reduced as manifested by the gradual change in deformation δ" in region 80 from the bearing surface 92, not in contact with platform surface T', to interior bearing surface 94 in contact with surface 82.

The stress concentration in region 80 thus increases prefereably in this embodiment a maximum of only about 25% as illustrated. This is a significant reduction in stress in the bearing 20 as compared to a 400% edge stress concentration of the prior art bearing arrangement of FIG. 1. While a 25% increase in stress concentration is illustrated in the present embodiment, other values, e.g., up to about 100% increase may be permissible in certain implementations. Since the taper of tapered surface T may be controlled to predetermined requirements, the 25% or even less increase in stress concentration is not a problem to achieve, and the lower the value the better the bearing edge wear performance of a given implementation.

A similar edge wiping configuration is associated with the patellar bearing 48 and patellar platform 50 of the patellar component 18, FIG. 2. Thus the patellar platform 50 surface edge 52 is also tapered with a tapered surface T similar to the tapering of the platform member 23 of FIG. 5.

Figure 6:
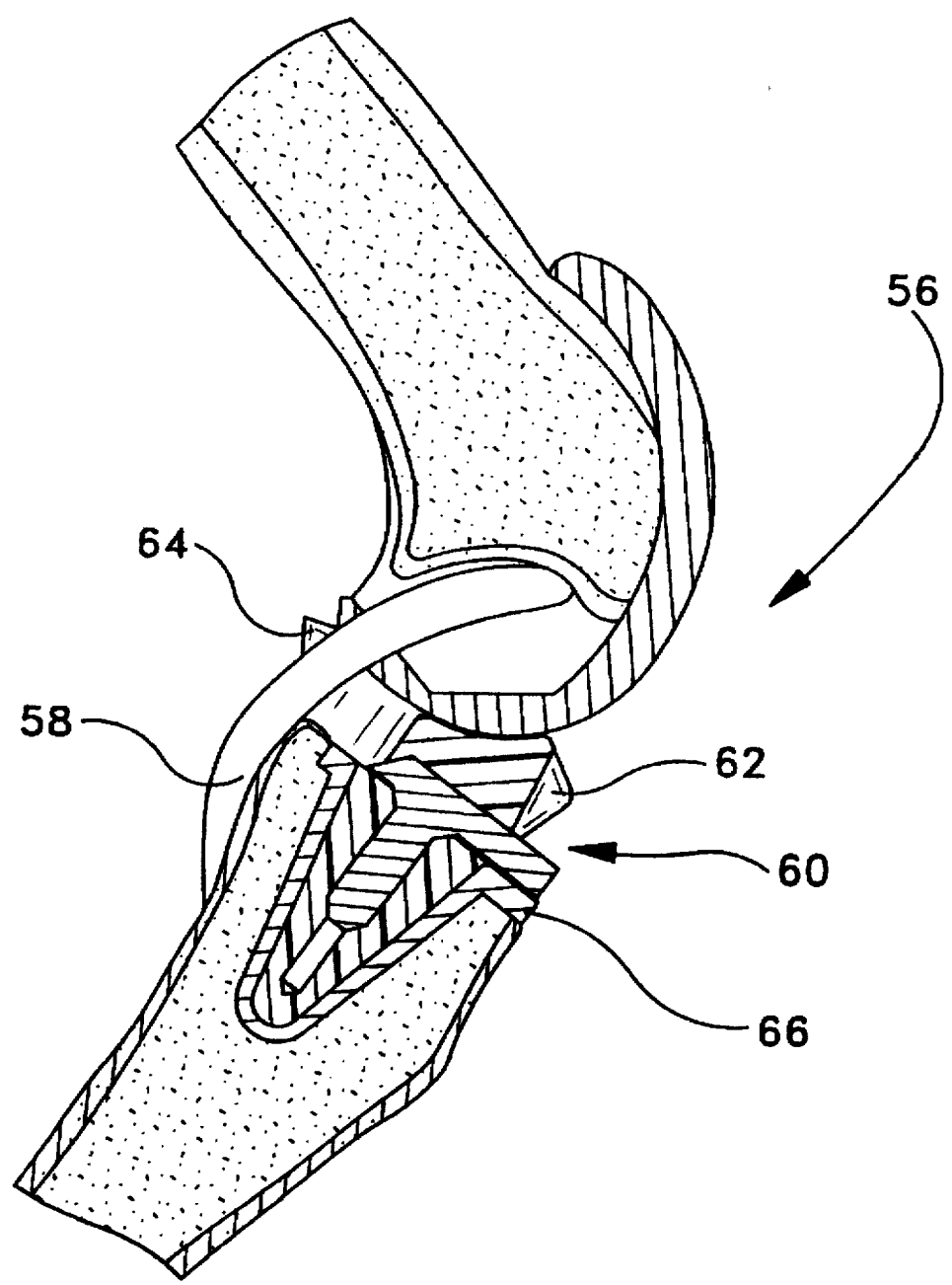
FIG. 6 is a side elevation sectional view of a knee and prothesis in a second embodiment of the present invention.
Figure 7:
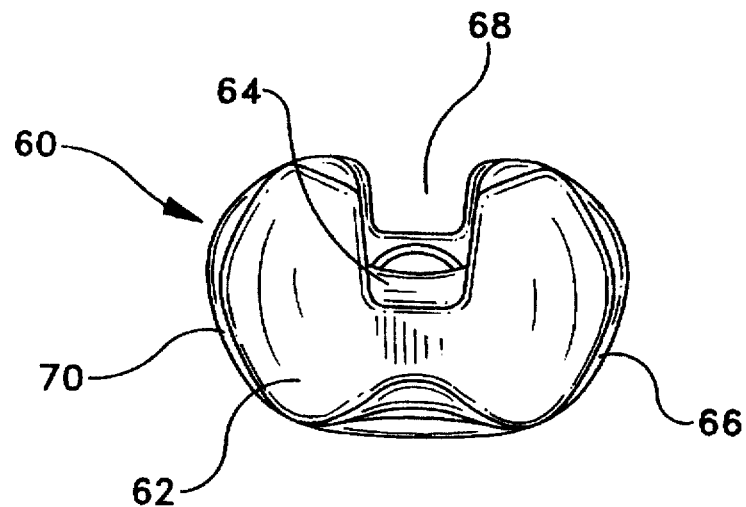
FIG. 7 is a plan view of the tibial bearing and platform components of the prothesis of FIG. 6.

The edge tapering described has another benefit. The embodiment of the tibial bearing 20 of FIGS. 3 and 4 is intended for use in a knee replacement where the posterior cruciate ligament of the knee 54, FIG. 2, is not retained. Where the posterior cruciate ligament 58 is retained in a knee 56, FIG. 6, an alternate embodiment knee replacement 60, shown in FIGS. 6 and 7, is used. In FIG. 6, a posterior cruciate retaining tibial bearing 62 has a posterior bearing notch 64 to clear the ligament 58. The associated tibial platform 66 has a posterior platform notch 68, FIG. 7, to accommodate the ligament 58.

To reduce tibial component inventory in a manufacturing environment, thus reduce costs, it is desirable to use the alternate tibial platform 66 for cases where the posterior cruciate ligament 58 is not retained. Thus it is desirable to use the tibial bearing 20, FIG. 2, with the alternate tibial platform 66, FIG. 6. In such cases, if an alternate tibial platform 66 with a prior art edge 42 as illustrated in FIG. 1 is used, the edge wiping effect of the notch 68, FIG. 7, would produce substantially increased, and unacceptable, wear on the planar tibial bearing 20 surface 28, FIG. 3. The use of an edge 70, FIG. 7, on platform 66 in the notch 68 with a tapered region 44, FIG. 8, will, however, produce only minor, and acceptable, increase in wear. Thus the use of a tapered edge 70 on the platform 66 allows the use of a common tibial platform for both bearing types of FIGS. 2–4, bearing 20 and FIGS. 6 and 7, bearing 62 (the latter with a notch 64) substantially reducing the amount and thus cost of inventory associated with a system for knee replacement. Further, the use of a common tibial platform 66, FIGS. 6 and 7, eliminates the possibility of the wrong platform being use with a particular bearing.

In FIG. 8, the tapered region 44 is a cylindrical surface (where the edge 34 is straight) or a toroidal surface (where the edge 34 is an arc) of width W, where the preferred taper radius $R_t$ of the cross section of the cylinder or toroid is very large compared to the normally used small radius $R_s$ at the platform corner. Finite element analysis of the tapered edge configuration and the prior art edge 42 of FIG. 1 shows a stress magnification of only about 25% for the tapered edge but an almost 400% stress magnification for the prior art edge 42 as discussed above. In most prothesis designs using articulating bearing and platform surfaces, the peak bearing pressures do not occur at the edge, thus a minor stress increase does not substantially increase overall surface damage. However, a four times increase in stress at the edge will, in most implementations, mean that the stresses at the edge significantly exceed those away from the edge and thus such a magnification will substantially increase overall surface damage.

The use of a prothesis according to the present invention can in most instances substantially eliminate the adverse effect of stress edge wiping allowing the development and use of improved designs of improved performance and an increased range of application. The present invention has wide applicability to the prosthetic art and can be applied to almost all replacement joints now in use including hips, ankles, shoulders, fingers, toes, and elbow.

It should be understood that modifications may be made to the disclosed embodiments by one of ordinary skill the disclosed embodiments are given by way of example and not limitation, the scope of the invention being defined by the appended claims.

What is claimed is:

1. In a prosthesis including a joint comprising first and second members each having a surface thereof articulating under load in contact with one another, the combination comprising:

a first member having a substantially planar first surface; and a second member having a substantially planar second surface including an edge, a side surface extending from said edge substantially orthogonal to said second surface, said second surface engaging the first surface in articulating contact such that said first surface and said second surface, including said edge thereof, are under compressive load during said articulating contact, said compressive load causing portions of said first member in engagement with the second member to exhibit a contact stress of at least a first value, said second surface having a gradual convex tapering region extending inwardly on said second surface from said edge a selected distance so as to cause the first member to exhibit an increased edge contact stress concentration in portions of the first member in engagement with the tapering region of the second member, said increased edge contact stress being of a second value which is no more than about twice said first value.

2. The combination of claim 1 wherein the second member is metal and the first member is a thermoplastic.

3. The combination of claim 1 wherein the first member is of a lower hardness than the second member.

4. The combination of claim 1, wherein the second surface at said gradual tapering region comprises a curvature which is tangential to portions of said second surface disposed interiorly from said tapering region.

5. The combination of claim 1 wherein the second surface at said gradual tapering region comprises a curvature of a plurality of contiguous tangential curves of differing radii.

6. The combination of claim 4 wherein the gradual tapering comprises at least one radius.

7. The combination of claim 1 wherein the second member has a side edge surface forming said edge with the second surface, the second surface at the gradual tapering region comprising a ramp gradually merging with the second surface at one ramp edge and terminating in a curve at the second member edge surface at an opposite ramp edge, the curve merging with said side edge surface.

8. The combination of claim 7 wherein the ramp is curved.

9. The combination of claim 1, wherein the second surface is configured for engaging the first surface in congruent articulating contact.

10. The combination of claim 1 wherein the tapered region approximates a radius of greater than 25 mm and extends inwardly from the edge an extent of at least about 2.5 mm.

11. The combination of claim 10 wherein the tapered region approximates a radius of at least about 50 mm and extends inwardly from the edge an extent of at least about 3.0 mm.

12. The combination of claim 1 wherein the tapered region terminates at said edge in a curved corner of radius $R_c$, said tapered region approximating a radius $R_t$, $R_t$ being substantially larger than $R_c$.

13. The combination of claim 1 wherein the tapered region is shaped such that the first surface exhibits a gradual deformation in the region of the first surface adjacent to said edge.

14. The combination of claim 1, wherein said second member further includes means for attachment to a bone at locations thereon spaced from said second surface, said combination further comprising a third member in articulating contact with portions of said first member spaced from said first surface thereof, said third member having means for attachment to another bone.

15. In a prosthesis including a joint comprising first and second members each having a surface thereof articulating under load in contact with one another, the combination comprising:

a first member having a first surface; and a second member having a second surface and a side edge surface forming an edge with the second surface, the second surface engaging the first surface in articulating contact such that said first surface and said second surface, including said edge thereof, are under compressive load during said articulating contact, said compressive load causing portions of said first member in engagement with the second member to exhibit a contact stress of at least a first value, said second surface having a gradually tapering region extending inwardly on said second surface from said edge a selected distance so as to cause the first member to exhibit an increased edge contact stress concentration on portions of the first member in engagement with the tapering region of the second member, said edge contact stress being of a second value which is no more than about twice said first value, the second surface at the gradual tapering region comprising a ramp gradually merging with portions of said second surface interiorly of said gradual tapering region at one ramp edge and terminating in a curve at the side edge surface of said second member to define an opposite ramp edge, the curve merging with said side edge surface wherein the ramp is planar and inclined relative to the interior regions of the second surface and to the side edge surface.

16. In a prosthesis including a joint comprising first and second members each having a surface articulating under load and in contact with one another, the combination comprising:

a thermoplastic first member having a substantially planar first surface; and a metallic second member having a substantially planar second surface engaging the first surface in articulating contact, the second surface having an edge, a side surface extending from said edge substantially orthogonal to said second surface, said second surface including said edge thereof being under compressive load with the first surface during said articulating contact, said second surface having a gradual tapering convex region adjacent to and extending inwardly from said edge of said second surface a distance so as to cause the first member to exhibit a gradual generally uniform rate of change of deformation in said first surface in response to said compressive load with said second surface, such that the deformation of said first surface varies uniformly from essentially zero at portions aligned with said edge to a maximum at portions of said first surface aligned with regions of said second surface spaced said distance inwardly from said edge of said second surface.

17. In a knee joint prosthesis comprising first and second surfaces in articulating load contact with one another, the combination comprising:

a thermoplastic tibial bearing having a substantially planar first surface; and a metal tibial component having a substantially planar second surface for engaging the first surface in articulating contact, the second surface having an edge, a side surface extending from said edge substantially orthogonal to said second surface, said second surface, including said edge thereof, being under compressive load with the first surface during said articulating contact, said second surface having a gradual tapering region adjacent to and extending inwardly from said edge of said second surface a distance W, said compressive load causing portions of said thermoplastic tibial bearing engaged with portions of said second surface spaced inwardly from said tapering region thereof to exhibit a contact stress of generally a first value, said gradual tapering region being configured so as to cause portions of the thermoplastic tibial bearing engaged therewith to exhibit edge stress concentration of a second value of no more than about twice said first value.

18. In a prosthesis including a joint comprising first and second surfaces in articulating load contact with one another, the combination comprising:

a thermoplastic bearing having a substantially planar first surface; and a metal member having a substantially planar second surface for engaging the first surface in articulating contact, the second surface having an edge, a side surface extending from said edge substantially orthogonal to said second surface, said second surface, including said edge thereof, being under compressive load with the first surface during said articulating contact, said second surface having a gradual tapering region adjacent to and extending inwardly from said edge of said second surface a distance, said compressive load causing regions of said bearing inwardly from said tapering region of said second surface of said metal member to exhibit a contact stress of generally a first value, the gradual tapering region of said second surface being configured to cause the bearing to exhibit edge stress concentration of a second value in a region of engagement of the edge of the second surface with the first surface, the second value in the first member being no more than about twice said first value.

19. The combination of claim 18 wherein the bearing and member are tibial components of a knee prothesis.

20. The combination of claim 18 wherein the bearing is UHMWPe and the member is metal.

21. The combination of claim 18 wherein the second value is about 25% greater than the first value.

22. The combination of claim 18 wherein the bearing and the metal member are patellar components of a knee prothesis.

23. The combination of claim 18 wherein said gradual tapering region comprises a curvature which is tangential with at least said second planar surface interior said edge.

24. In a knee joint prosthesis comprising first and second surfaces in articulating load contact with one another, the combination comprising:

a thermoplastic patellar bearing having a first surface; and a metal patellar component having a second surface for engaging the first surface in articulating contact, the second surface having an edge, said second surface, including said edge thereof, being under compressive load with the first surface during said articulating contact, said second surface having a gradual tapering region adjacent to and extending inwardly from said edge of said second surface a distance W, said compressive load causing portions of said thermoplastic patellar bearing engaged with portions of said second surface spaced inwardly from said tapering region thereof to exhibit a contact stress of generally a first value, said gradual tapering region being configured so as to cause portions of the thermoplastic patellar bearing engaged therewith to exhibit edge stress concentration of a second value of no more than about twice said first value.

* * * * *